(12) United States Patent
Brub (10) Patent No.: US 9,750,507 B2
(45) Date of Patent: Sep. 5, 2017

(54) EMERGENCY TOURNIQUET DEVICES AND ASSOCIATED METHODS OF USE AND MANUFACTURE

(75) Inventor: Darrin Brub, Honolulu, HI (US)

(73) Assignee: HAWAII PRODUCT DEVELOPMENT, INC., Honolulu, HI (US)

( * ) Notice: Subject to any disclaimer, the term of this patent is extended or adjusted under 35 U.S.C. 154(b) by 1577 days.

(21) Appl. No.: 13/397,166

(22) Filed: Feb. 15, 2012

(65) Prior Publication Data
US 2012/0215254 A1 Aug. 23, 2012

Related U.S. Application Data

(60) Provisional application No. 61/444,487, filed on Feb. 18, 2011.

(51) Int. Cl.
*A61B 17/00* (2006.01)
*A61B 17/132* (2006.01)

(52) U.S. Cl.
CPC ............. *A61B 17/1327* (2013.01)

(58) Field of Classification Search
CPC ........... A61B 17/132; A61B 17/1322; A61B 17/1325; A61B 17/1327; A61B 5/02233; A61B 5/02241; Y10T 24/4016; Y10T 24/4072; Y10T 24/4077; Y10T 24/4736; Y10T 29/511; Y10T 408/67;
(Continued)

(56) References Cited

U.S. PATENT DOCUMENTS 1,234,818 A * 7/1917 Sturrock ............... A44B 11/10
24/196
1,447,967 A * 3/1923 Davis ..................... A44B 11/25
24/163 R
(Continued)

FOREIGN PATENT DOCUMENTS

GB 291600 A * 6/1928
WO WO 2012112665 A1 8/2012

OTHER PUBLICATIONS

PCT Notification of Transmittal of International Search Report with Written Opinion for PCT/US2012/025213 dated Aug. 22, 2012 (related to present application) PCT/US2012/025213 filed Feb. 15, 2012 and its entire file history.

*Primary Examiner* — Jonathan Miles
*Assistant Examiner* — Kankindi Rwego
(74) *Attorney, Agent, or Firm* — Optima Law Group, APC; Thomas E. Jurgensen (57) ABSTRACT

Tourniquet devices and associated methods of use and manufacture are disclosed herein. Tourniquet devices configured in accordance with several embodiments of the disclosure can include, for example, a strap having a proximal end portion and a distal end portion, a buckle assembly connected to the proximal end portion, and a pulley assembly movably coupled to the strap. Tourniquet devices configured in accordance with the technology can be easily applied because the pulley assemblies can reduce the force a user must exert on the tourniquet devices to constrict or occlude blood flow. Additionally, tourniquet devices disclosed herein can also serve as functional, wearable items (e.g., a belt, integrated into clothing) such that the tourniquet devices are conveniently stored and readily accessible in emergencies.

15 Claims, 7 Drawing Sheets

(58) Field of Classification Search
CPC ..... A44B 11/005; A44B 11/006; A44B 11/02; A44B 11/12; A44B 11/125; A44B 11/2592
See application file for complete search history.

(56) References Cited

U.S. PATENT DOCUMENTS

| | | | |
|---|---|---|---|
| 4,005,506 A * | 2/1977 | Moore | A44B 11/12 128/DIG. 15 |
| 5,500,959 A * | 3/1996 | Yewer, Jr. | A61F 5/028 2/311 |
| 6,884,254 B2 | 4/2005 | Brooks | |
| 7,604,651 B1 * | 10/2009 | Harris | A41D 13/1236 606/203 |
| 2003/0028215 A1 | 2/2003 | Brooks | |
| 2007/0088385 A1 | 4/2007 | Perry | |
| 2008/0183207 A1 | 7/2008 | Horne | |
| 2010/0057120 A1 | 3/2010 | Kirkham | |
| 2011/0295309 A1 * | 12/2011 | Sullivan | A44B 11/005 606/203 |

* cited by examiner

EMERGENCY TOURNIQUET DEVICES AND ASSOCIATED METHODS OF USE AND MANUFACTURE

CROSS REFERENCES

This application claims priority from U.S. Provisional Patent Application No. 61/444,487 filed Feb. 18, 2011 incorporated herein in its entirety by this reference.

TECHNICAL FIELD

The present technology is related to medical devices. In particular, the present disclosure is related to tourniquet devices and associated methods of use and manufacture.

BACKGROUND

Tourniquets are devices that can control venous and arterial circulation to extremities. In operation, tourniquets apply pressure circumferentially upon skin and underlying tissues of a limb. The pressure transfers to the walls of vessels, causing them to compress, constrict, and become temporarily occluded. To avoid further injury to the limb, the tourniquet pressure should be sufficient to stop blood flow, but should not be strong enough to damage tissue, nerves, and/or blood vessels.

In general, tourniquets are categorized as either surgical tourniquets or emergency tourniquets. Tourniquets used during surgery allow surgeons to work on limbs in a bloodless setting, and accordingly include specialized instruments to gauge the correct pressures for specific applications. Surgical tourniquets, for example, are generally pneumatic devices that include pressure gauges, electrical inflation mechanisms, sensors, and/or outer devices suitable for hospital settings. In contrast, tourniquets used in emergency settings are used to prevent severe blood loss prior to a victim reaching a state of shock and prior to hospital care. Thus, emergency tourniquets are configured to facilitate easy and quick application to stop blood flow from a limb prior to more intensive hospital care.

Emergency tourniquets are especially advantageous in military settings, where pre-hospital care is critical. During combat, for example, explosions (e.g., improvised explosive devices) and gun fire can result in traumatic injuries that require immediate occlusion of blood flow. Additionally, formal medical care may not be readily available in combat situations. Thus, emergency tourniquets are often stored on military personnel and/or in military vehicles to ensure tourniquets are available when traumatic bleeding injuries occur. However, military personnel generally carry heavy gear (e.g., weaponry, backpacks, water containers, etc.) when in combat, making the additional storage of a tourniquet inconvenient. Additionally, tourniquets stored in military vehicles may be difficult to access after an injury causing event because the vehicle may be difficult to reach and/or retrieval of the tourniquet may be impractical due to damage to the vehicle.

BRIEF SUMMARY OF THE INVENTION

The present invention specifically addresses and alleviates the above mentioned deficiencies, more specifically, the present invention is directed to a simple, fast and effective tourniquet device that can be quickly deployed and used in the field, including by the wounded soldier if need be. The tourniquet devices and methods of use according to the present invention are configured in embodiments that include and comprise, for example, a strap having a proximal end portion and a distal end portion, a buckle assembly connected to the proximal end portion, and a pulley assembly movably coupled to the strap. Tourniquet devices configured in accordance with the technology can be easily applied because the pulley assemblies can reduce the force a user must exert on the tourniquet devices to constrict or occlude blood flow. Additionally, tourniquet devices disclosed herein can also serve as functional, wearable items (e.g., a belt, integrated into clothing) such that the tourniquet devices are conveniently stored and readily accessible in emergencies and have multiple other field uses, including, e.g., gun straps, backpack straps, seat belts and as restraint devices.

Accordingly, in a first aspect, the present invention provides a tourniquet device comprising a strap having a proximal end portion and a distal end portion, a buckle assembly connected to the proximal end portion of the strap, and a pulley assembly slidably coupled to the strap and movable between the proximal end portion and the distal end portion, the pulley assembly having a support member and a pulley member rotatably coupled to the support member. In a preferred embodiment, the strap has a width sufficient to apply pressure to constrict blood flow, while preventing constricting blood flow to the point of injury or amputation.

In a further aspect, the buckle assembly a frame for connecting the end portion of the strap, and in a preferred embodiment, can include a second pulley member coupled to the frame to bias the buckle assembly away from the injured limb.

In another aspect, the size of the plurality of openings is proportional to the weight of the flexible material.

In yet a further aspect, the pulley mechanism includes a clamping member to allow free movement of the strap in one direction and restricted movement in the opposite direction.

In a further aspect, the pulley attachment mechanism allows for incremental loosening and tightening of the tourniquet device and selective reattachment to the distal end of the strap as pressure in increased or decreased.

In another aspect of the present invention, a method of applying a tourniquet devices according to the present invention is provided, comprising the steps of encircling a limb above the point of blood loss with a tourniquet device comprising:

a strap having a proximal end portion and a distal end portion;

a buckle assembly connected to the proximal end portion of the strap; and a pulley assembly slidably coupled to the strap and movable between the proximal end portion and the distal end portion, the pulley assembly having a support member and a pulley member rotatably coupled to the support member; and looping the distal end portion of the strap through the buckle assembly to reverse directions, looping the distal end portion of the strap through the pulley member, applying sufficient pressure to constrict blood flow by pulling the distal end of the strap away from the pulley assembly to tension the strap, transferring circumferential pressure to the limb, and releasably securing the distal end portion to an attachment mechanism.

While the tourniquet devices and methods will be described for the sake of grammatical fluidity with functional explanations, it is to be expressly understood that the claims, unless expressly formulated under 35 USC 112, or similar applicable law, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112, or similar applicable law. The invention can be better visualized by turning now to the following drawings wherein like elements are referenced by like numerals.

DETAILED DESCRIPTION

The present technology is directed to tourniquet devices and associated methods of use and manufacture. A tourniquet device configured in accordance with several embodiments of the disclosure can include, for example, a strap having a proximal end portion and a distal end portion, a buckle assembly connected to the proximal end portion, and a pulley assembly movably coupled to the strap. In operation, the strap can be routed around a limb and through the buckle assembly. From there, the strap can reverse direction such that the strap routes around at least a portion of the limb a second time and passes through the pulley assembly. A user can then apply a force to the distal end portion of the strap to tighten the tourniquet device around the limb, and the distal end portion of the strap can be secured in place with an attachment mechanism once a sufficient occlusive pressure is applied to the limb. When not in use, the tourniquet device can be worn (e.g., as a belt or restraint, integrated into clothing, etc.), such that the tourniquet device is conveniently stored, easily accessible in emergencies, and quickly applied to injuries. It will be appreciated that several of the details set forth below are provided to describe the following embodiments in a manner sufficient to enable a person skilled in the relevant art to make and use the disclosed embodiments. Several of the details described below, however, may not be necessary to practice certain embodiments of the new technology. Additionally, the new technology can include other embodiments that are within the scope of the claims but are not described in detail with reference to FIGS. 1-7.

Many of the details, dimensions, angles and other features shown in the Figures are merely illustrative of particular embodiments of the invention. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings. Accordingly, other embodiments can have other details, dimensions, angles and features without departing from the spirit or scope of the present disclosure. In addition, identical reference numbers are used in the Figures to identify identical or at least generally similar elements. To facilitate the discussion of any particular element, the most significant digit or digits of any reference number refers to the Figure in which that element is first introduced. For example, element 110 is first introduced and discussed with reference to FIG. 1.

Figure 1:
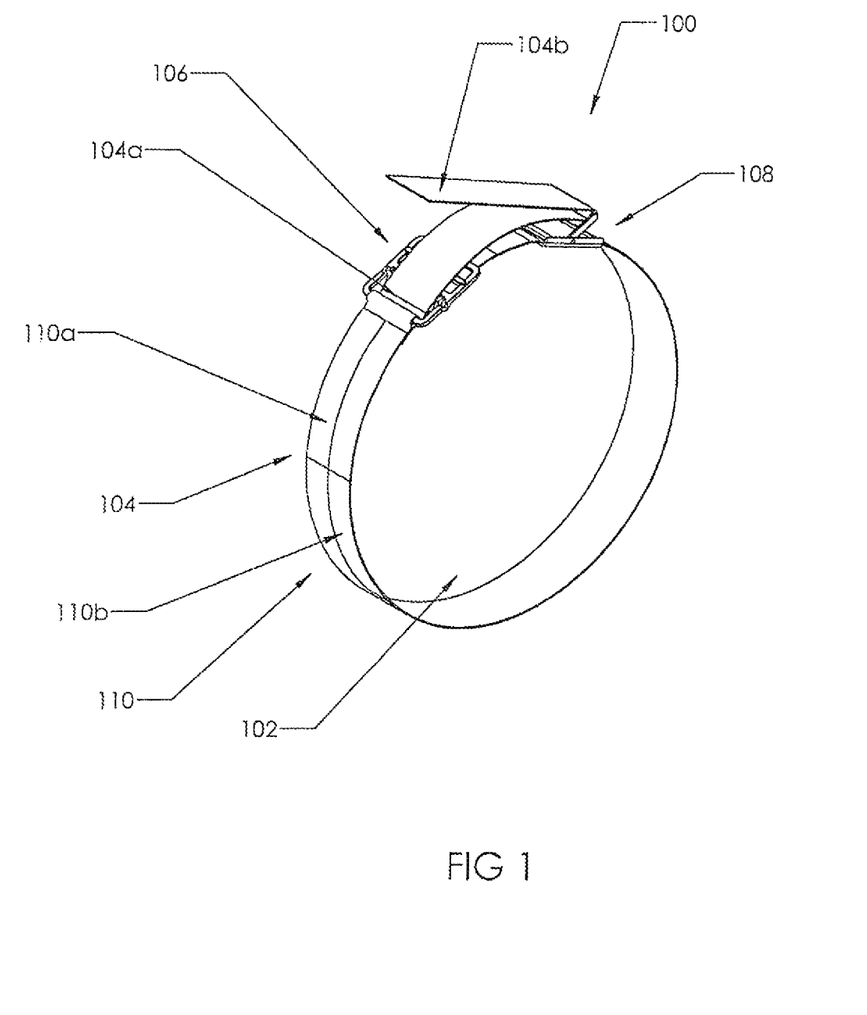
FIG. 1 is a perspective view of a tourniquet device secured around a limb in accordance with embodiments of the new technology.

FIG. 1 is a perspective view of a tourniquet device 100 being tensioned around a person's limb 102 in accordance with embodiments of the new technology. The tourniquet device 100 can include a strap 104, a buckle assembly 106, and a pulley assembly 108. The buckle assembly 106 can be secured to a proximal end portion 104a of the strap 104, and the pulley assembly 108 can be movably coupled to the strap 104 such that the pulley assembly 108 can move along a length of the strap 104 to accommodate differently sized limbs (e.g., arms, legs, etc.). For example, the pulley assembly 108 can be moved closer to the buckle assembly 106 for smaller limbs (e.g., arms), and farther from the buckle assembly 106 for larger limbs (e.g., legs). Additionally, the pulley assembly 108 can be positioned along the strap 104 to gain additional leverage when tensioning the tourniquet device 100.

The strap 104 can have a diameter D that can apply sufficient pressure to constrict or occlude blood flow from the limb 102, while preventing the strap 104 from constricting the limb to the point of injury and/or amputation. In some embodiments, for example, the strap 104 can have a diameter of three inches. In other embodiments, the strap 104 can have a smaller diameter, a larger diameter, or vary in diameter. The strap 104 can be made from woven nylon (e.g., webbing), leather, plastic, rubber, cotton, and/or another suitable material that can withstand tension forces sufficient to cut off blood flow.

The tourniquet device 100 can further include an attachment mechanism 110 that can releasably secure a free portion (e.g., the distal end portion 104b) of the strap 104 to the tourniquet device 100. As shown in FIG. 1, the attachment mechanism 110 can be strips of Velcro® (one strip visible in FIG. 1) spaced along a circumference of the strap 104 at 110a and 110b. In other embodiments, the attachment mechanism can be a snap, a clip, and/or another suitable attachment mechanism that can releasably secure the strap 104 to the tourniquet device 100.

In some embodiments, the pressure applied by the tourniquet device 100 to the limb 102 can be slowly and/or partially released to prevent damage to the limb 102 (e.g., gangrene), sudden blood loss, and/or renewed bleeding. Thus, the attachment mechanism 110 can be configured to allow for incremental loosening of the tourniquet device 100 and reattachment at each incremental pressure decrease. For example, the attachment mechanism 110 can include a plurality of fasteners (e.g., Velcro® strips) spaced around the strap 104 at 110a and 110b and/or a releasable fastener (e.g., a clip) that allow the strap 104 to be re-secured to the attachment mechanism 110 during each incremental pressure decrease. Similarly, the attachment mechanism 110 can also be used to incrementally increase pressure.

In an emergency, the tourniquet device 100 can completely encircle the limb 102 above the point of blood loss (e.g., a bullet hole). The distal end portion 104b of the strap 104 can be routed through the buckle assembly 106, looped around the buckle assembly 106, where the strap 104 can reverse direction. The strap 104 can at least partially encircle the limb 102 for a second time such that the distal end portion 104b can be routed through and around the pulley assembly 108. The distal end portion 104b of the strap can be pulled away from the pulley assembly 108 to tension the strap 104. The tension can transfer to the limb 102 such that the tourniquet device 100 applies circumferential pressure to the limb 102 to constrict or occlude blood flow from above the tourniquet device 100. The pulley assembly 108 can approximately double the force exerted by a user on the tourniquet device 100 to the limb 102. For example, if an occlusive pressure is X, the user need only exert approximately X/2 to adequately tension the tourniquet device 100 around the limb 102 and cut off blood flow. Once a desired pressure is reached (e.g., enough pressure to stop bleeding), the attachment mechanism 110 can releasably secure the distal end portion 104b of the strap 104 to the tourniquet device 100. If desired, the pressure to the limb 102 can be released incrementally by reducing the tension on the strap 104 and re-securing the strap 104 to the attachment mechanism 110. In operation, the tourniquet device 100 multiplies the force exerted by the user such that the tourniquet device 100 can be applied with one hand and can be used constrict or occlude the user's own blood flow. This can be especially advantageous when the user is injured and/or lacks the strength or dexterity necessary to achieve occlusive pressure. Advantageously, the tourniquet 100 device can also be used as a sling for a broken arm. For example, a user can encircle the strap 104 around his or her neck, and secure the strap at a desired length using the buckle assembly 106, the pulley assembly 108, and/or the attachment mechanism 110. The user can then support his or her arm with the strap 104. Additionally, the tourniquet device 100 can also be used to secure a splint in place by wrapping the strap 104 around the limb and the splint and tightening the tourniquet device 100 using the pulley assembly 108 and/or the buckle assembly 106. Moreover, the tourniquet device 100 can find a wide variety of other uses consistent with the present invention and of those skilled in the art, including: being tied around a person's body and/or limbs to restrain the person (e.g., in combat situations), used to create an emergency evacuation litter, as a gun strap to carry a gun and can be used to create a backpack or as backpack straps or compression straps on a backpack. The tourniquet device 100 can also be used as tie down straps, towing straps, as a climbing harness, as a fixed loop for helicopter rescue, as an animal (e.g. dog) harness, animal leash, animal collar or animal restraint.

Figure 2:
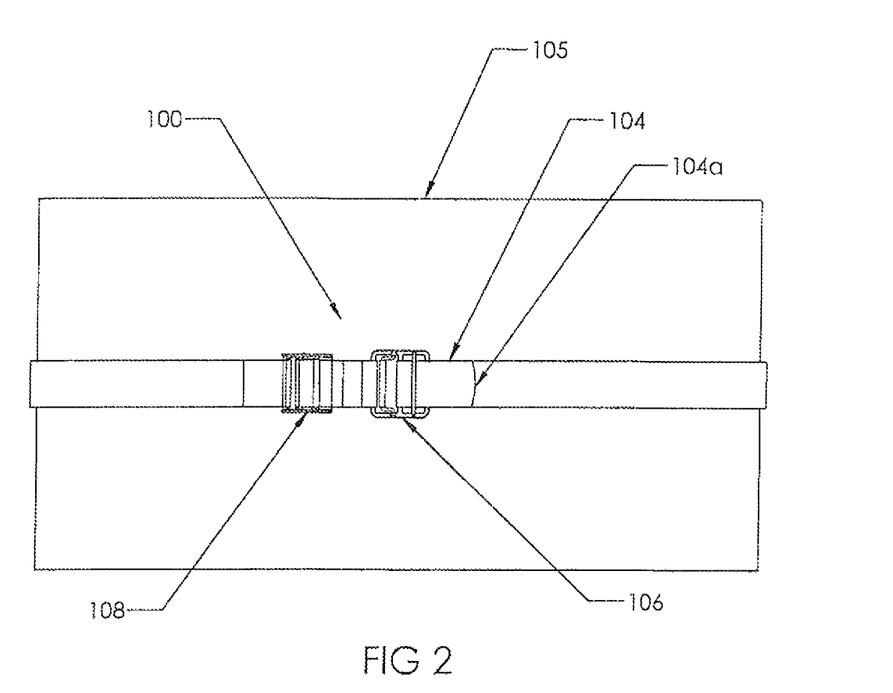
FIG. 2 is a front view of the tourniquet device shown in FIG. 1 worn as a belt in accordance with the new technology.

When the tourniquet device 100 is not in use, the tourniquet device 100 can be worn for convenient storage and quick accessibility. For example, FIG. 2 is a perspective view of the tourniquet device 100 shown in FIG. 1 worn as a belt in accordance with the new technology. The tourniquet device 100 can be looped around a torso 105, through belt loops 103, and can be secured using the buckle assembly 106. The pulley assembly 108 can be moved along the length of the strap 104 such that the pulley assembly 108 to secure a loose end (e.g., the distal end portion 104b) in place. In an emergency, the tourniquet device 100 can quickly be removed from the torso 105 and secured around the limb 102. Thus, when the tourniquet device 100 is not in use, the tourniquet device 100 can serve an additional functional purpose (e.g., a belt) that does not require additional storage. In other embodiments, the tourniquet device 100 can be worn and/or used with another article of clothing or accessory, such as a back pack strap.

In further embodiments, the tourniquet device 100 can be integrated into clothing at select locations (e.g., upper limb portions). For example, the tourniquet device 100 can encircle an upper thigh portion in each leg of a pair of pants and a detachable fabric portion can cover the strap 104, the buckle assembly 106, and/or the pulley assembly 108 for unobtrusive storage. In an emergency, a wearer must only remove the fabric portion to access and employ the tourniquet device 100 on his or her leg. Thus, the tourniquet device 100 can be conveniently stored around a limb for quick application in emergencies. In still further embodiments, the tourniquet device 100 can be integrated into or used as a vehicle restraint (e.g., a seat belt) and detached from the vehicle for use as a tourniquet.

Figure 3A:
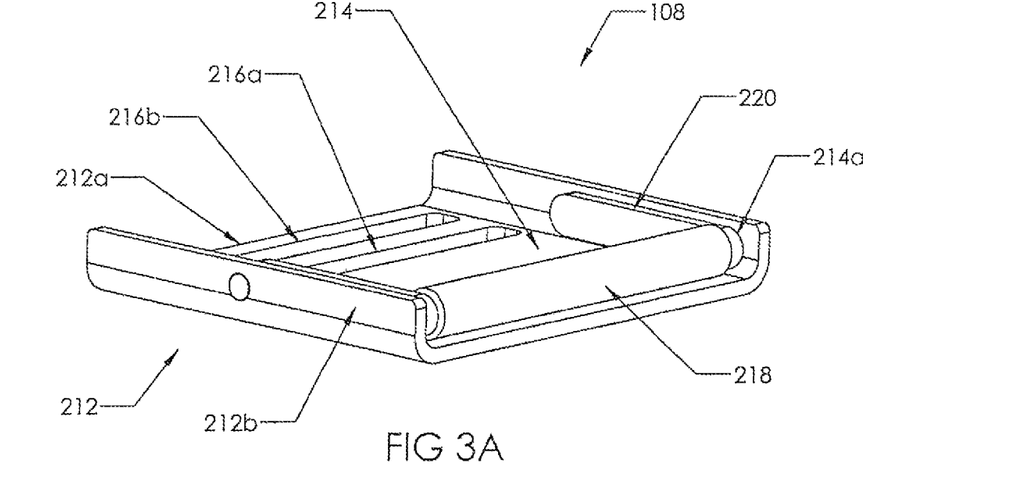
FIGS. 3A and 3B is an enlarged isometric view of a pulley assembly configured in accordance with embodiments of the new technology.
Figure 3B:
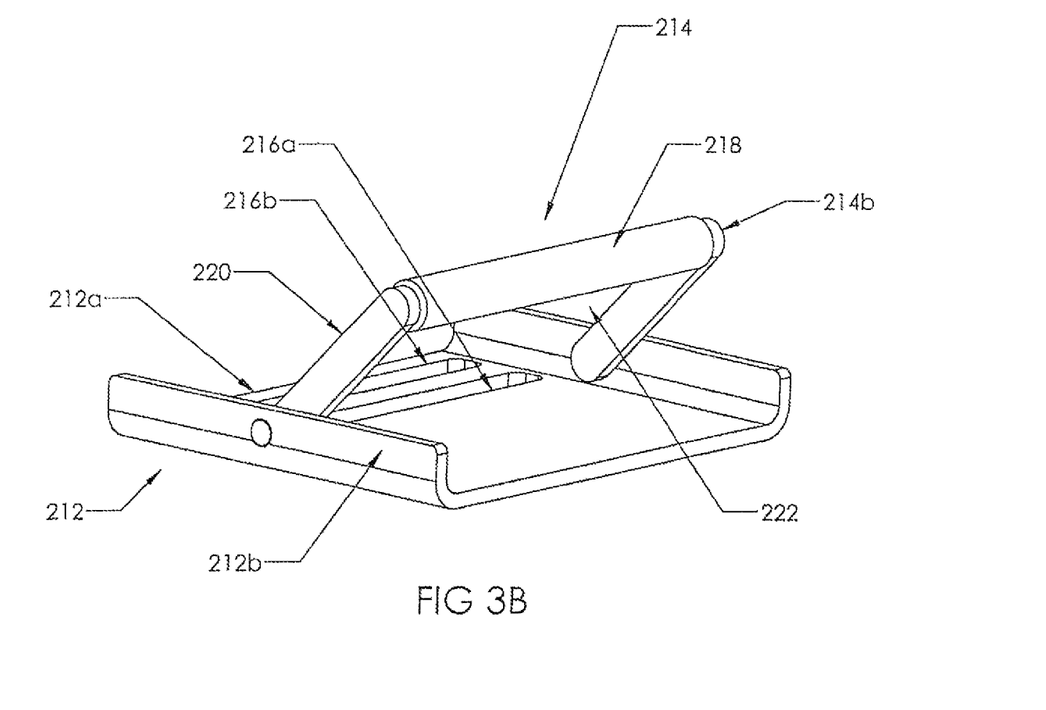

FIG. 3 is an enlarged isometric view of the pulley assembly 108 shown in FIG. 1. The pulley assembly 108 can include a support member 212 and a pulley member 214 (shown at a first position 214a and at a second position 214b) rotatably connected to the support member 212. The support member 212 can include a first surface 212a and a second surface 212b opposite the first surface 212a. In the embodiment illustrated in FIG. 3, the support member has a substantially rectangular shape that has generally similar dimensions as the strap 104 (shown in FIG. 1) and curved portions that can enclose a portion of the pulley assembly 108. In other embodiments, the support member 212 can have different shapes suitable for supporting the pulley member 214.

As shown in FIG. 3, the support member 212 can further include apertures 216 (identified individually as a first aperture 216a and a second aperture 216b) extending through the support member 212. The apertures 216 can be sized to receive the strap 104, and slidably attach the pulley assembly 108 to the strap 104. In some embodiments, for example, the distal end portion 104b of the strap 104 can be routed from the second surface 212b, through the first aperture 216a, across a portion of the first surface 212a between the apertures 216, and through the second aperture 216b. In other embodiments, the strap 104 can be woven through the apertures 216 in the opposite direction and/or the support member 212 can include more or less apertures 216 sized to receive the strap 104.

The slidable attachment provided by the apertures 216 allows the pulley assembly 108 to move along the length of the strap 104 such that the position of the pulley assembly 108 can change to accommodate differently sized limbs and/or provide better leverage to the user. When the pulley assembly 108 is at a desired position, the apertures 216 can substantially restrict the movement of the pulley assembly 108 to prevent it from moving as the tourniquet device 100 is tensioned. Additionally, as described with reference to FIG. 2, the slidable attachment provided by the apertures 216 allows the pulley assembly 108 to be moved when the tourniquet device 100 is used as a belt to secure loose, free end portions of the strap 104.

In other embodiments, the support member 212 can include other fasteners that allow the pulley assembly 108 to move along the length of the strap 104 to accommodate differently sized limbs and/or torsos. For example, in some embodiments, the support member 212 can include a clip having a push button that, when engaged, allows the pulley assembly 108 to move along the length of the strap 104 and, when released, substantially secures the pulley assembly 108 in the desired position. In further embodiments, the support member 212 can include clips, snaps, and/or other suitable fasteners that slidably and/or releasably secure the pulley assembly 108 to the strap 104. In still further embodiments, the pulley assembly 108 can be detachable from the tourniquet device 100 when not in use and secured with a clip and/or other suitable fastener in an emergency.

The pulley member 214 can include a roller portion 218 rotatably coupled to a hinged portion 220 such that the roller portion 218 can spin 360° about the hinged portion 220. As shown in the embodiment in FIG. 2, the hinged portion 220 can extend through the roller portion 218 to serve as a spindle for the roller portion 218. In other embodiments, the hinged portion 220 can be rotatably coupled to end portions of the roller portion 218. The hinged portion 220 can be rotatably coupled to the support member 212 with hinges, pins, and/or other suitable devices that allow the pulley member 214 to rotate.

In some embodiments, the pulley member 214 can be biased by a spring force and/or include a locking mechanism to move the pulley member 214 to specified positions. For example, the pulley member can be locked at an angle (e.g., 45°, 90°) away from the support member 212 while tensioning the tourniquet device 100 for optimal leverage on the strap 104. As another example, the pulley member 214 can be biased toward the support member 212 such that the pulley member 214 is compactly stored when not in use. In other embodiments, the pulley member 108 can further include a cover (not shown) that encloses the pulley member 214 when it is not in use to prevent the pulley member 214 from catching on surroundings.

As shown in FIG. 3B, the hinged portion 220 and the roller portion 218 can form an opening 222 such that the strap 104 can be routed around the roller portion 218. The roller portion 218 can have a length L that is at least the diameter D (shown in FIG. 1A) of the strap 104 such that the roller portion 218 can provide a contact point for the strap 104 when the tourniquet device 100 is tensioned. The roller portion 218 can be made from materials having low coefficients of friction to allow the strap 104 to smoothly glide over the roller portion 218. In some embodiments, for example, the roller portion 218 can be made from smooth plastics, metals, and/or other substantially frictionless materials. Additionally, the entire pulley member 214 (e.g., the roller portion 218 and the hinged portion 220) can be made from a material able to withstand the forces applied to the pulley assembly 108 without substantial deformation. For example, the pulley member 214 can be made from metals, strong plastics, and/or other suitable materials.

As illustrated by the arrow in FIG. 3A, the pulley member 214 can rotate with respect to the support member 212 from the first position 214a to the second position 214b. In the first position 214a, the pulley member 214 can be substantially flush and/or parallel to a first surface 212a of the support member 212. The pulley member 214 can be rotated to the first position 214a for compact storage when the tourniquet device 100 is not in use. Additionally, the pulley member 214 can be placed in the first position 214a to secure a free end portion of a strap 104 under the pulley member 214. In the second position 214b, the pulley member 214 can rotate away from the first surface 212a of the support member 212. The pulley member 214 can be moved to the second position 214b during use as a tourniquet such that the strap 104 can be routed through the opening 222 and around the roller portion 218 to tension the strap 104 around a limb (e.g., the limb 102 described in FIG. 1). In other embodiments, the pulley member 214 can rotate beyond the second position 214b, and/or rotate freely 180° from the first position 214b to be proximate to the apertures 216 at the first surface 212a. In further embodiments, the pulley member 214 can rotate more or less with respect to the support member 212.

In selected embodiments, the pulley assembly 108 can also include a clamp mechanism that can (1) tension the tourniquet device 100 tighter around a limb as a user pulls more of the strap 104 through the clamp mechanism, and (2) retain that tension when the user releases the strap 104. For example, the clamp can allow the strap 104 to pass substantially freely in one direction (e.g., tightening the tourniquet device 100) and can substantially prevent the strap 104 from passing in the opposite direction (e.g., loosening the tourniquet device 100). In additional embodiments, the clamp mechanism can also include a release feature, such as a button, knob, or other suitable manual or electronic release, that can be used to loosen the strap 104 from the clamp mechanism.

The pulley member 214 can reduce the amount of force required to attain a requisite pressure. For example, the pulley member 214 can reduce the force required by approximately half. This is especially helpful when the user applying the tourniquet device 100 is wounded himself and/or lacks the strength to apply the appropriate amount of pressure to slow or occlude bleeding.

Figure 4:
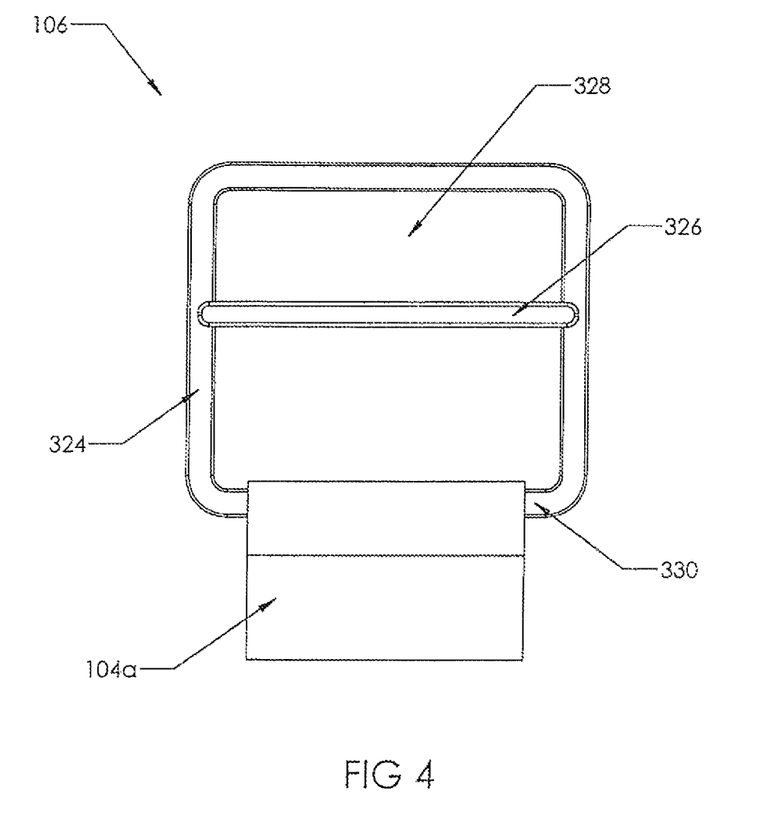
FIG. 4 is an enlarged top view of a buckle assembly configured in accordance with embodiments of the new technology.

FIG. 4 is an enlarged top view of the buckle assembly 106 shown in FIG. 1. The buckle assembly 106 can include a frame 324 and a post 326. As shown in FIG. 4, the frame 324 can form an opening 328 such that the proximal end portion 104a of the strap 104 can be secured around a back portion 330 (shown in hidden lines) of the frame 324. The proximal end portion 104a can be attached around the back portion 330 with thread, snaps, glue, and/or other suitable fasteners that can secure the proximal end portion 104a to the frame 324. In other embodiments, the proximal end portion 104a of the strap 104 can be integrally formed.

The post 326 can extend across the opening 328, substantially parallel to the back portion 330 of the frame 324. In some embodiments, the post 326 can be slidably attached to the frame 324 such that the post 326 can adjust the width of the opening 328 to secure the strap 104. In other embodiments, the post 326 can be fixedly attached to the frame 324 and/or the frame 324 and the post 326 can be a single piece. The frame 324 and the post 326 can be made from semi-rigid and/or rigid materials that can withstand the force applied to the tourniquet device 100 to occlude blood flow. For example, in some embodiments, the frame 324 and the post 326 can be made from steel alloys, strong plastics, and other suitable materials.

In operation, the distal end portion 104b of the strap 104 can be routed through the opening 328, and the strap 104 can be looped around the post 326 and/or the frame 324 such that the strap 104 encircles a limb. If used as a belt, the distal end portion 104b can be woven around the buckle assembly 106 like a conventional box-frame belt buckle.

Figure 5:
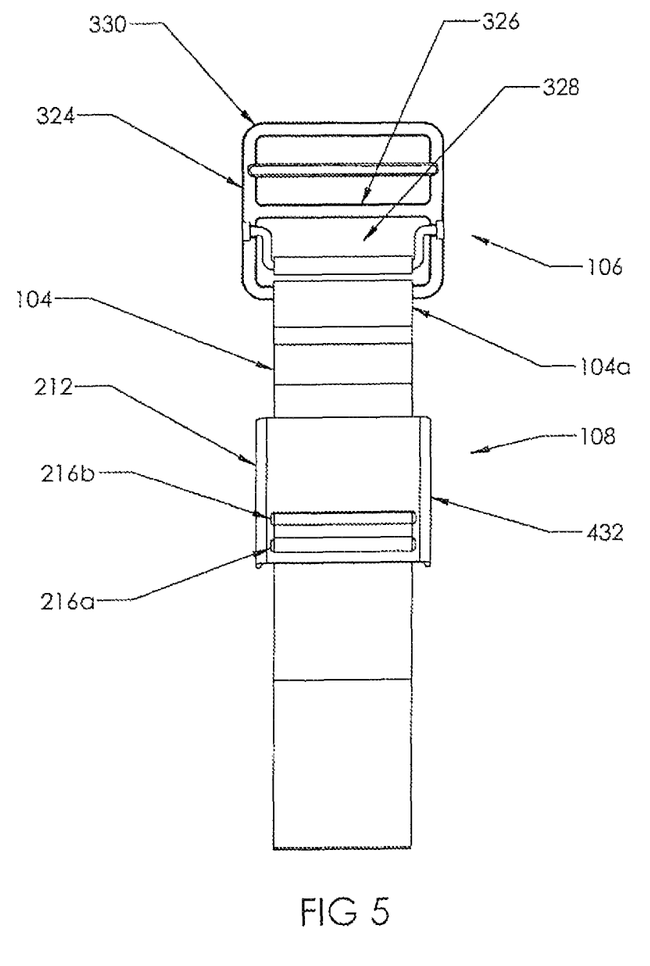
FIG. 5 is an enlarged back view of a portion of the tourniquet device shown in FIG. 1 in accordance with embodiments of the new technology.

FIG. 5 is an enlarged back view of the buckle assembly 106 and the pulley assembly 108 shown in FIGS. 1-4. In the illustrated embodiment, the proximal end portion 104a of the strap 104 is secured to the back portion 330 of the frame 324. The post 326 extends across the opening 328 formed by the frame 324 such that the distal end portion 104b (not visible) of the strap 104 can be woven through the buckle assembly 106. The pulley assembly 108 can be slidably attached to the strap 104 by weaving the strap through the apertures 216. In the embodiment illustrated in FIG. 3, the hinged portion 220 of the pulley member 214 is attached to the support member 212 with pins 432 (not visible) that allow the pulley member 214 to pivot with respect to the support member 212. Additionally, FIG. 1 shows the attachment mechanism 110 includes strips of Velcro® (shown individually as a first attachment mechanism 110a and a second attachment mechanism 110b) spaced along the strap 104 such that the tourniquet device 100 can be incrementally tightened or loosened.

Figure 6A:
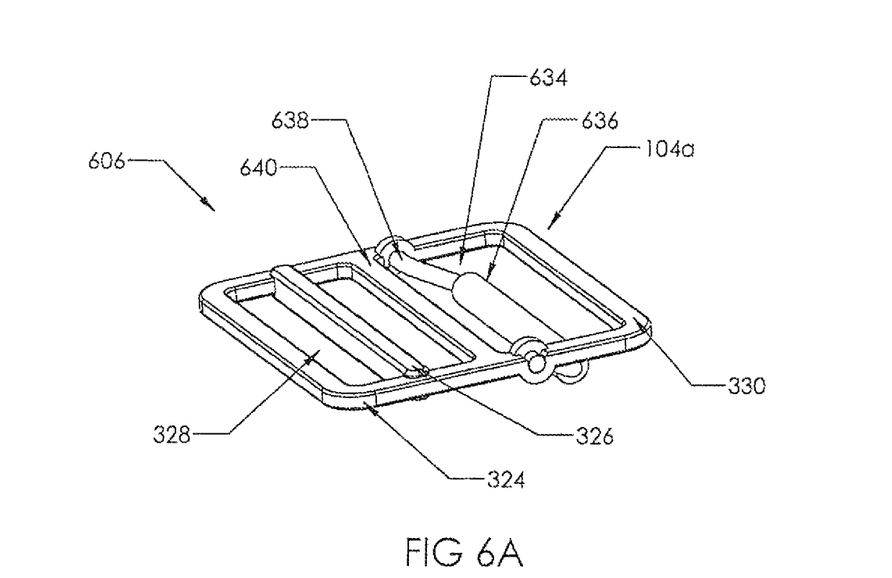
FIG. 6A is an isometric view of a buckle assembly configured in accordance with other embodiments of the new technology.
Figure 6B:
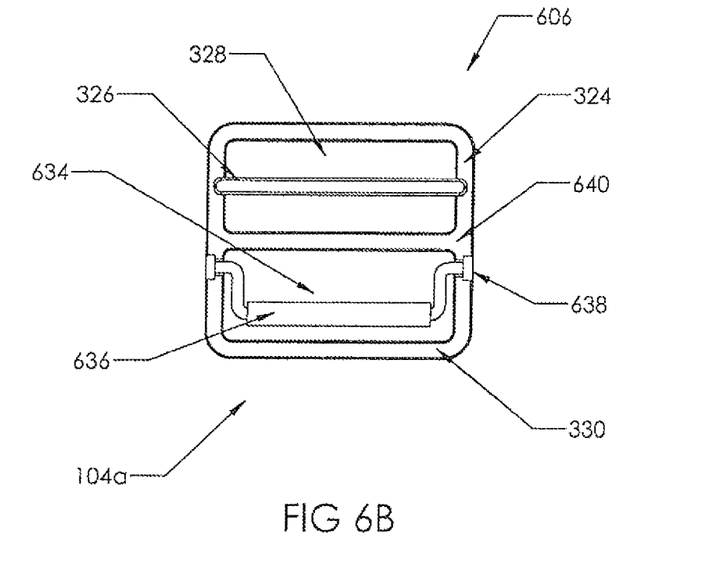
FIG. 6B is a top view of the buckle assembly shown in FIG. 6A.

FIGS. 6A and 6B are isometric and top views, respectively, of a buckle assembly 606 configured in accordance with other embodiments of the new technology. The buckle assembly 606 includes features generally similar to the buckle assembly 106 described with reference to FIG. 4. For example, the buckle assembly 606 includes the frame 324, the post 326, and the opening 328 across which the post 326 extends. The back portion 330 of the frame 324 can be coupled to the proximal end portion 104a of the strap 104.

In the embodiment illustrated in FIGS. 6A and 6B, the buckle assembly 606 can further include a second pulley member 634. The second pulley member 634 can include features generally similar to the pulley member 214 described in FIG. 2. For example, the second pulley member 634 can include a roller portion 636 and a hinged portion 638 that are at least generally similar to the roller and hinged portions 218 and 220 described above. In the embodiment shown in FIGS. 6A and 6B, the second pulley member 634 further includes a reinforcement member 640 that extends across the opening 328 and provides support for the second pulley member 634 when the strap 104 is tensioned around it. The reinforcement member 640 can be substantially parallel to the post 326. In other embodiments, the second pulley member 634 second does not include the reinforcement member 640, while in further embodiments the buckle assembly 606 includes additional reinforcement members 640.

As shown in FIG. 6A, the second pulley member 634 can extend downwardly away from the frame 324 such that the second pulley member 634 biases the buckle assembly 606 away from a limb (e.g., the limb 102 described above). The biased pulley member 634 can prevent the buckle assembly 606 from pinching skin on the limb during tensioning of the tourniquet device 100. When the buckle assembly 606 is not in use, the second pulley member 634 can retract toward the frame 324 as shown in FIG. 6B. In some embodiments, the second pulley member 634 can be biased further away from and/or closer toward the frame 324 than shown in FIGS. 5A and 5B. In other embodiments, the second pulley member 634 can rotate about the frame 324, and can be secured in desired positions using suitable locking mechanisms. In further embodiments, the second pulley member 634 can be freely hinged about the frame 324 and/or another portion of the buckle assembly 606. In still further embodiments, the second pulley member 634 can be attached in a fixed position to a portion of the buckle assembly 606.

Figure 7:
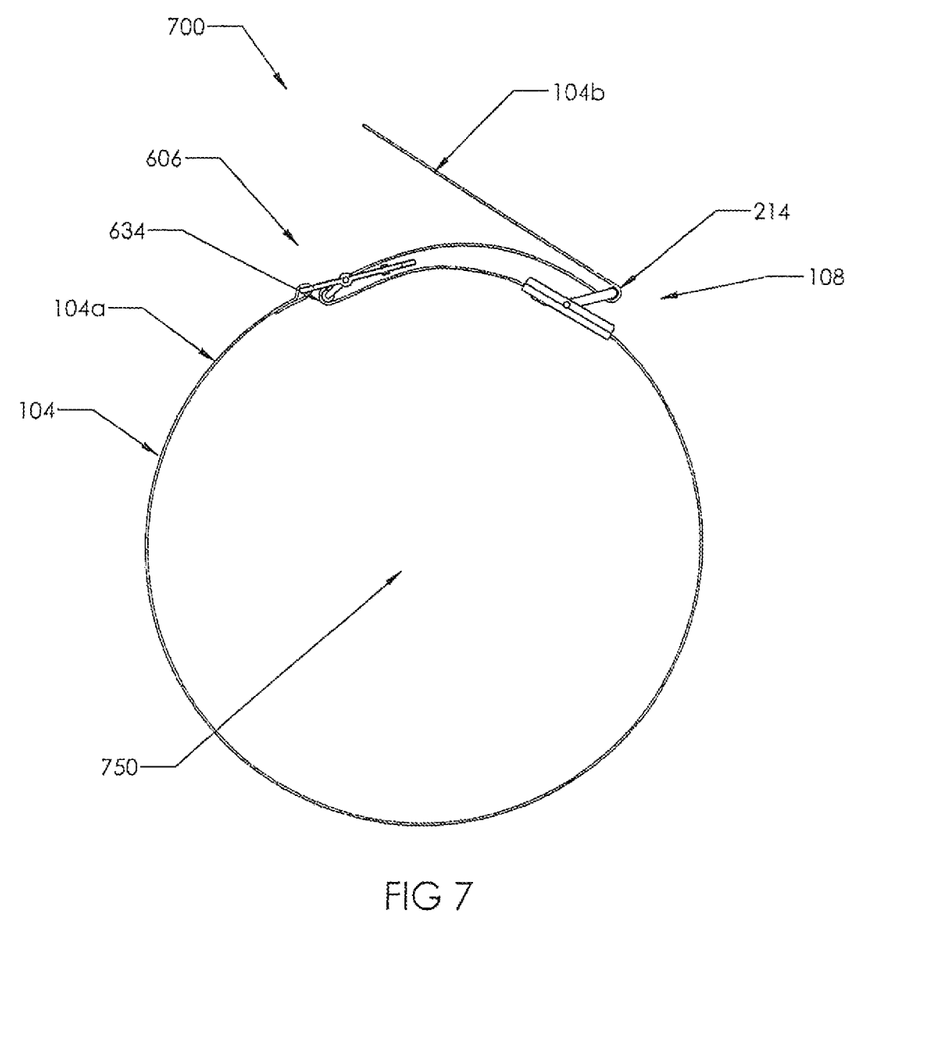
FIG. 7 is a side view of a tourniquet device configured in accordance with further embodiments of the new technology.

FIG. 7 is a side view of the tourniquet device 700 in accordance with further embodiments of the new technology. The tourniquet device 700 can include features generally similar to the tourniquet device 100 described in FIG. 1. For example, the tourniquet device includes the strap 104, the pulley assembly 108 having the support member 212 and the pulley member 214. Additionally, the tourniquet device 700 includes the buckle assembly 606 described in FIGS. 6A and 6B that includes a pulley. Thus, the tourniquet device 700 shown in FIG. 7 includes two pulleys: one on the pulley assembly 108 and another on the buckle assembly 606. Advantageously, this double-pulley tourniquet device 100 can require even less force from a user to constrict or occlude blood flow.

As shown in FIG. 7, the tourniquet device 700 can form an opening 750 through which a limb can extend. The distal end portion 104b of the strap 104 can be routed through the buckle assembly 606 and around the second pulley member 634. The second pulley member 634 can bias the buckle assembly 606 away from the skin to ensure the limb is not pinched when tensioning the tourniquet device 700. The addition of the second pulley member 634 to the tourniquet device 700 can also reduce the amount of force exerted by the user to adequately tension the tourniquet device 700. For example, the strap 104 can slide easily over the buckle assembly 606, creating less friction, and thus requiring less force to obtain occlusive pressure.

As further shown in FIG. 7, the distal end portion 104b can be redirected to surround at least a portion of the limb a second time. The distal end portion 104b can then extend through the opening 222 formed by the pulley member 214 of the pulley assembly 108. The tourniquet device 700 can be tensioned around the limb by pulling on the distal end portion 104b of the strap 104. In the embodiment illustrated in FIG. 7, the pulley member 214 is locked in place an angle away from the support member 212 when the tourniquet device 700 is tensioned to provide better leverage.

From the foregoing, it will be appreciated that specific embodiments of the present technology have been described herein for purposes of illustration, but that various modifications may be made without deviating from the technology. For example, in the embodiments illustrated in FIG. 1, the pulley assembly 108 is positioned near the buckle assembly 106. However, the pulley assembly 108 can be positioned anywhere along the strap 104 to achieve maximal leverage. Additionally, padding can be added to the tourniquet devices 100, 700 (e.g., on the strap 104, on the support member 212) described in FIGS. 1-7 to provide additional comfort for an injured person. Certain aspects of the new technology described in the context of particular embodiments may also be combined or eliminated in other embodiments. For example, the tourniquet devices 100, 700 described in FIGS. 1-7 can include additional pulley members and/or additional pulley assemblies. Further, while advantages associated with certain embodiments of the new technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A tourniquet device, for a primary use encircling a patient's limb and a secondary use worn as a belt looped around a wearer's torso, the tourniquet device comprising:
   a strap having a proximal end portion and a distal end portion; wherein the strap has a width sufficient to apply pressure to constrict blood flow, while preventing constricting blood flow to the point of injury/amputation;
   a first buckle assembly connected to the proximal end portion of the strap;
   a second pulley assembly slidably coupled to the strap and movable between the proximal end portion and the distal end portion, the second pulley assembly having first and second apertures passing therethrough, the second pulley assembly located at a distance from the first buckle assembly;

the second pulley assembly having a pulley assembly support member and a first pulley member rotatably coupled to the pulley assembly support member and biased away from the pulley assembly support;

the first buckle assembly having a frame for connection to the proximal end portion of the strap and forming an opening wherein at least one post extends across the opening;

the first buckle assembly further having a second pulley member rotatably coupled to the frame, the second pulley member rotating away from the frame;

the strap passing through the first and second apertures of the second pulley assembly and then about the second pulley of the first buckle assembly;

whereby a pulley having a two-to-one force multiplication is formed by the first and second pulleys and the strap passing between them;

and further whereby a limb opening is formed through which in a first such usage, such limb may extend and be encircled and in a second such usage such tourniquet device may be worn as a belt.

2. The tourniquet device of claim 1, the first pulley extends away from the pulley assembly support member and the limb opening; but wherein the second pulley extends downwardly from the frame into the limb opening.

3. The tourniquet device of claim 1, wherein the second pulley member includes a pulley reinforcement support reinforcement member extending across the opening and provides support for the second pulley member.

4. The tourniquet device of claim 1, wherein the pulley assembly support is configured to include at least one aperture for slidably attaching the pulley assembly to the strap.

5. The tourniquet device of claim 1, wherein both the pulley members include a roller portion rotatably coupled to a hinged portion.

6. The tourniquet device of claim 1, wherein the pulley member includes a clamping mechanism configured to allow the strap to pass substantially freely in one direction and substantially preventing the strap from passing in the opposite direction.

7. The tourniquet device of claim 1, further comprising an means for attaching for releasably securing the distal end portion of the strap to the tourniquet device.

8. The tourniquet device of claim 7, wherein the means for attaching is configured to allow for incremental loosening or tightening of the tourniquet device and reattachment of the distal end to the strap at each incremental pressure decrease or increase as applied to a limb.

9. The tourniquet device of claim 1, wherein the device is configured for wearing or storing in a form selected from a member of the group consisting of a belt, a backpack strap, integrated as part of a piece of clothing, and integrated as part of a vehicle.

10. The tourniquet device of claim 1, wherein the device can function as a device selected from the group consisting of a device, restraint, and securing device for a splint.

11. A tourniquet device for usage on a part of a patient's body, the tourniquet device comprising:

a strap having a proximal end portion and a distal end portion wherein the strap has a width sufficient to apply pressure to constrict blood flow, while preventing constricting blood flow to the point of injury/amputation;

a pulley assembly slidably coupled to the strap and movable between the proximal end portion and the distal end portion, the pulley assembly having a pulley assembly support and a first pulley member rotatably coupled to the pulley assembly support;

a buckle assembly including a second pulley member rotatably coupled to a frame and connected to the proximal end portion of the strap, the frame forming an opening wherein at least one post extends across the opening;

the strap passing about the first pulley and then about the second pulley, the distal end projecting from the second pulley;

whereby a pulley having a two-to-one force multiplication is formed by the first and second pulleys and the strap passing between them;

and further whereby a limb opening is formed through which such part of such patient's body may extend; and a means for attaching for releasably securing the distal end portion of the strap to the tourniquet device.

12. The tourniquet device of claim 11, wherein the means for attaching attachment mechanism is configured to allow for incremental loosening or tightening of the tourniquet device and reattachment of the distal end to the strap at each incremental pressure decrease or increase as applied to a limb.

13. The tourniquet device of claim 12, wherein the means for attaching is hook-and-loop fabric.

14. A method of applying a tourniquet device, comprising the steps of i) encircling a limb above the point of blood loss with a tourniquet device comprising:

a strap having a proximal end portion and a distal end portion, wherein the strap has a width sufficient to apply pressure to constrict blood flow, while preventing constricting blood flow to the point of injury/amputation a buckle assembly connected to the proximal end portion of the strap; and a pulley assembly slidably coupled to the strap and movable between the proximal end portion and the distal end portion, the pulley assembly having a pulley assembly support and a pulley member rotatably coupled to the pulley assembly support;

ii) looping the distal end portion of the strap through the buckle assembly to reverse directions;

wherein the buckle assembly of step ii) further comprises a second pulley member rotatably coupled to a frame and wherein the looping of the distal end portion of the strap is through the second pulley member;

iii) then looping the distal end portion of the strap through the first pulley member;

whereby a pulley having a two-to-one force multiplication is formed by the first and second pulleys and the strap passing between them;

iv) applying sufficient pressure to constrict blood flow by pulling the distal end of the strap away from the pulley assembly to tension the strap, transferring circumferential pressure to the limb; and v) releasably securing the distal end portion to an means for attaching.

15. The method of claim 14, wherein the pressure applied to the limb is incrementally reduced or increased by releasing the distal end portion from the means for attaching and resecuring the strap to the means for attaching at an incremental position equivalent to a reduction or increase in pressure to the limb.

* * * * *